(12) United States Patent
Frank

(10) Patent No.: US 7,589,634 B2
(45) Date of Patent: Sep. 15, 2009

(54) AUXILIARY ANTENNA ARRAY FOR SYSTEM FOR DETECTING FOREIGN OBJECTS IN A SURGICAL PATIENT

(75) Inventor: Milton Frank, Bergenfield, NJ (US)

(73) Assignee: Med-Track Partners LLC, Waldwick, NJ (US)

( * ) Notice: Subject to any disclaimer, the term of this patent is extended or adjusted under 35 U.S.C. 154(b) by 320 days.

(21) Appl. No.: 11/656,148

(22) Filed: Jan. 22, 2007

(65) Prior Publication Data
US 2008/0174409 A1 Jul. 24, 2008

(51) Int. Cl.
G08B 13/14 (2006.01)
G08B 21/00 (2006.01)

(52) U.S. Cl. .................. 340/572.1; 340/686.2
(58) Field of Classification Search ............. 340/572.1, 340/686.2, 686.3, 686.4, 870.01; 705/2, 705/150
See application file for complete search history.

(56) References Cited

U.S. PATENT DOCUMENTS 6,094,173 A * 7/2000 Nylander .................. 343/742
6,107,921 A * 8/2000 Eberhardt et al. ......... 340/572.7
7,307,530 B2 * 12/2007 Fabian et al. ............. 340/572.1
7,420,468 B2 * 9/2008 Fabian et al. ............. 340/572.1
2005/0149358 A1 * 7/2005 Sacco et al. .................... 705/2
2006/0066453 A1 * 3/2006 Homanfar et al. ......... 340/686.2
2006/0202827 A1 * 9/2006 Volpi et al. ............... 340/572.1
2008/0018432 A1 * 1/2008 Volpi et al. ................. 340/10.3

* cited by examiner

Primary Examiner—Benjamin C Lee
Assistant Examiner—Sigmund Tang
(74) Attorney, Agent, or Firm—Robert L. Epstein; Epstein Drangel Bazerman & James, LLP

(57) ABSTRACT

The apparatus includes a hand-held RF transducer having a transmit section for providing an energizing signal to cause a RFID tag associated with an object retained in the body of the patient to transmit an RF signal and a receiver section for receiving the RF signal transmitted by the RFID tag, as the patient's body is scanned. An auxiliary antenna array for receiving the transmitted RF signal transmitted by the RFID tag is situated in the mattress on the operating table under the patient. Signal processing electronics are connected to the receiver section of the transducer and to the auxiliary antenna array for determining and indicating when a RF signal from a tag has been received, representing that a tagged object remains in the body of the patient, and for decoding the RF signal to identify the object.

34 Claims, 5 Drawing Sheets

AUXILIARY ANTENNA ARRAY FOR SYSTEM FOR DETECTING FOREIGN OBJECTS IN A SURGICAL PATIENT

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A "SEQUENCE LISTING", A TABLE, OR A COMPUTER PROGRAM LISTING APPENDIX SUBMITTED ON COMPACT DISC

Not Applicable

BACKGROUND OF THE INVENTION

1. Field of the Invention

The present invention relates to RFID (radio frequency identification) tagging systems and more particularly, to a auxiliary antenna array for increasing the range of a RFID system for detecting foreign objects in a surgical patient wherein the auxiliary antenna array consists of pairs of antennae and associated electronics placed in a mattress situated on top of an operating table.

2. Description of Prior Art Including Information Disclosed Under 37 CFR 1.97 and 1.98

The problem of leaving foreign objects, such as surgical instruments and sponges, in patients after surgery has been of great concern ever since modern surgery began. A foreign object present in a patient after surgery can lead to illness or death. Further, it also raises serious medical malpractice issues.

Accordingly, various systems have been tried to prevent foreign objects from being left off in patents after surgery. Such systems include manually or automatically counting the surgical instruments and sponges used in a surgical procedure before and after surgery and comparing the counts to insure that all instruments and sponges used in the procedure are accounted for. However, such systems do not produce completely satisfactory results as they are dependant upon human beings for accuracy and human beings are prone to make errors, especially when functioning under pressure or adverse conditions.

Metal objects, such as surgical instruments, can be detected by X-ray or other scanning techniques. However, such detection systems require costly and expensive equipment, pose a danger to unprotected personnel, and subject patients to potentially harmful radiation. Further, some systems, such as x-ray scanners, are unable to detect non-metallic objects.

RFID tagging has also been suggested for use in tracking and counting surgical instrument and sponges. Radio frequency identification (RFID) tags emit a radio frequency signal when excited by electromagnetic energy from a transmitting antenna. The emitted signal can include a coded identification number that represents a particular object, such as a surgical instrument or sponge. The emitted signal is received by a receiving antenna and processed by a computer to decode the identification number. The identification number is unique to a particular object and there permits automated tracking of all objects utilized during surgery with great accuracy once the RF signal from the excited tag is received.

One of the benefits of such a system is that it is non-evasive. The body of the patient can be quickly and easily scanned at the end of the surgical procedure to ensure all tagged instruments and sponges have been removed form the patient. The scanning can be performed by a conventional hand-held device or wand that contains a transmitting antenna, a receiving antenna, signal processing circuitry and a display or other audible or visual indicating device.

However, conventional systems of this type are not entirely reliable because they do not always receive the RF signal from the tag. They therefore require repeated scanning of the body at close range and in different orientations to provide reliable results. Properties of RFID tags that effect instrument scanning are: (a) the maximum distance between antenna and RFID tag is a function of the frequency of the signal; (b) signal attenuation due to water and soft tissue in the body is inversely dependant upon the frequency of the signal; (c) the received signal is strongest when the tag is perpendicular to the movement of the receiving antenna; (d) the metal of surgical instruments tends to block radio frequency waves; and (e) the size of the RFID tag is a function of the frequency of the emitted signal.

Those properties necessitate the use of small, low frequency RFID tags for detecting objects such as surgical instruments or sponges in the body. However, even when those types of RFID tags are utilized, successful scanning of the tag is limited by patient size and instrument orientation. Finding a retained instrument or sponge in the body requires scanning the patient multiple times and changing the antenna orientation for each scan. Accordingly, conventional equipment utilizing RFID tags for detecting the presence of foreign objects in a patient after surgery have not proved to be totally satisfactory.

The present invention greatly improves the success rate for detecting a retained instrument or sponge, utilizing small, low frequency RFID tags, by utilizing auxiliary receiving antennae to increase the ability of the system to receive the signal transmitted from the RFID tag. The antennae are situated in an array that is preferably mounted within a standard size mattress pad adapted to be situated beneath the patient on the operating table. The pad may be a single unit or consist of one or more removable sections to facilitate patient placement for various surgical procedures. The pad contains multiple receiving antennae arranged in pairs and associated electronics.

The mattress pad with the auxiliary antenna array replaces the pad normally used on an operating table. Before the surgical procedure begins, each of the instruments and sponges in the room is provided with an encoded RFID tag. The patient lies on top of the pad as in any surgical procedure. At the end of the procedure, before the incision is closed, the patient is scanned with a hand-held transducer containing both a transmitting antenna and receiving antenna, along with processing circuitry.

The transmitting antenna in the transducer generates a signal that excites any RFID tag in the body, which then emits a radio frequency signal. The signal generated by the RFID tag is received by the receiving antenna in the transducer and/or by one or more of the receiving antennae of the auxiliary antenna array within the pad below the patient. The auxiliary antenna array greatly increases the ability of the system to receive the RFID signal from the tagged object, regardless of the orientation of the surgical instrument or sponge within the body, or patient size, without the necessity for multiple scans.

It is, therefore, a prime object of the present invention to provide an improved system for detecting foreign objects in a patient after surgery.

It is another object of the present invention to provide an RFID tagging system for detecting foreign objects in a patient utilizing an auxiliary antenna array to increase the ability of the system to receive a signal from the RFID tagged object.

It is another object of the present invention to provide a system for detecting foreign objects in a patient on an operating table that utilizes small, low frequency RFID tags.

It is another object of the present invention to provide a system for detecting foreign objects in a patient on an operating table that reduces the necessity for scanning the patient multiple times using different antenna orientations.

It is another object of the present invention to provide a system for detecting foreign objects in a patient on an operating table that utilizes an auxiliary antenna array situated in a mattress pad of the type normally used on an operating table.

BRIEF SUMMARY OF THE INVENTION

In accordance with one object of the present invention, apparatus is provided for detecting an RFID tagged object in the body of a patient. The apparatus includes RF transducer means including means for energizing the tag to transmit an RF signal. Means located remotely from the RF transducer means are provided for receiving the transmitted RF signal from the tag. Signal processing means are operably connected to the RF signal receiving means for processing the output of the RF signal receiving means to determine when an RF signal from the tag has been received.

The apparatus also includes RF signal receiving means associated with the RF transducer means. The RF transducer means preferably takes the form of a hand-held scanner.

The RF signal receiving means associated with the transducer means and the remote RF signal receiving means are located on opposite sides of the body for best results.

Means operably connected to the signal processing means are provided for indicating the receipt of a RF signal from the tag. The indicating means may generate an audible or a visible signal.

The tag is a small, low frequency RFID tag.

The tag transmits a coded signal. The signal processing means includes means for decoding the signal to identify the detected object.

The apparatus includes a mattress pad within which the remote RF signal receiving means is located. The remote RF signal receiving means includes at least one pair of RF signal receiving antennae. A decoder is operably connected to the RF signal receiving antennae in the pair.

Preferably, the remote RF signal receiving means includes first and second pairs of RF signal receiving antennae. First and second decoders are provided. Each of the first and second decoders is respectively operably connected to a different pair of RF signal receiving antennae.

The remote RF signal receiving means includes an antenna array. The array includes a plurality of toroidal antennae. The antennae are situated in rows. The antennae rows are substantially parallel.

The antenna array is preferably located in the upper portion of a mattress pad.

In accordance with another aspect of the present invention, apparatus is provided for detecting an RFID tagged object in the body of a patient. The apparatus includes RF transducer means comprising means for energizing the tag to transmit an RF signal and first means for receiving said transmitted RF signal. Second means for receiving the transmitted RF signal is provided. Signal processing means operably connected to the first RF signal receiving means and said second RF signal receiving means are also provided for determining when a RF signal from the tag has been received.

The transmitted RF signal includes an identification code. The signal processing means includes means for decoding the identification code.

The RF transducer means takes the form of a hand-held scanner.

The first RF signal receiving means and the second RF signal receiving means are located on opposite sides of the body.

The apparatus also includes means operably connected to the signal processing means for indicating receipt of a RF signal from the tag.

The tag is a small, low frequency RFID tag.

The apparatus further includes a mattress pad within which the second RF signal receiving means is located.

The second RF signal receiving means includes a pair of RF signal receiving antennae. The RF signal receiving means includes a decoder operably connected to the RF signal receiving antennae in the pair.

The second RF signal receiving means preferably includes first and second pairs of RF signal receiving antennae. The RF signal receiving means includes first and second decoders. Each of the first and second decoders is respectively operably connected to a different pair of RF signal receiving antennae.

The second RF signal receiving means includes an antenna array. The array includes a plurality of toroidal antennae. The antennae are situated in rows. The antennae rows are substantially parallel.

The antenna array is located in the upper portion of a mattress pad.

Preferably, the first RF signal receiving means includes first and second oppositely oriented substantially identical antennae connected in series.

BRIEF DESCRIPTION OF THE SEVERAL VIEWS OF DRAWINGS

To these and such other objects that may hereinafter appears, the present invention relates to an auxiliary antenna array for a system for detecting foreign objects in a surgical patient as described in detail in the following specification and recited in the annexed claims, taken together with the accompanying drawings, in which like numerals refer to like parts and in which:

DETAILED DESCRIPTION OF THE INVENTION

There are several types of RFID systems, some working at high frequencies (megahertz range) and others at low frequencies. Generally, inventory systems use the high frequency RFID tags because of the long range and ability to store and send larger chunks of data. For systems used to track animals or for use in humans, low frequency tags (100-200 KHz) are used because high frequency signals are greatly attenuated by animal or human tissue. Also, high frequency tags cannot be used directly on metal instruments because the metal tends to absorb the high frequency RF signals. For those reasons, the present invention uses low frequency RFID tags.

In the low frequency system used in the present system, the RF tag has both a receiving coil and a transmitter coil. A pulsed transmitter in the RF transducer sends out a short burst of low frequency RF energy (128 KHz), which is received by the tag. The tag converts this energy to DC power, and in conjunction with the 128 Khz signal sends out a code by dividing the 128 Khz by 2 (64 Khz), which then uses PSK modulation to transmit a unique identification number. A sensitive receiver, tuned to the 64 KHz signal, filters out all other frequencies and amplifies the 64 KHz signal. In conjunction with a sync signal from the transmitter, the receiver detects and demodulates the received signal and recovers the transmitted identification number data.

Figure 1:
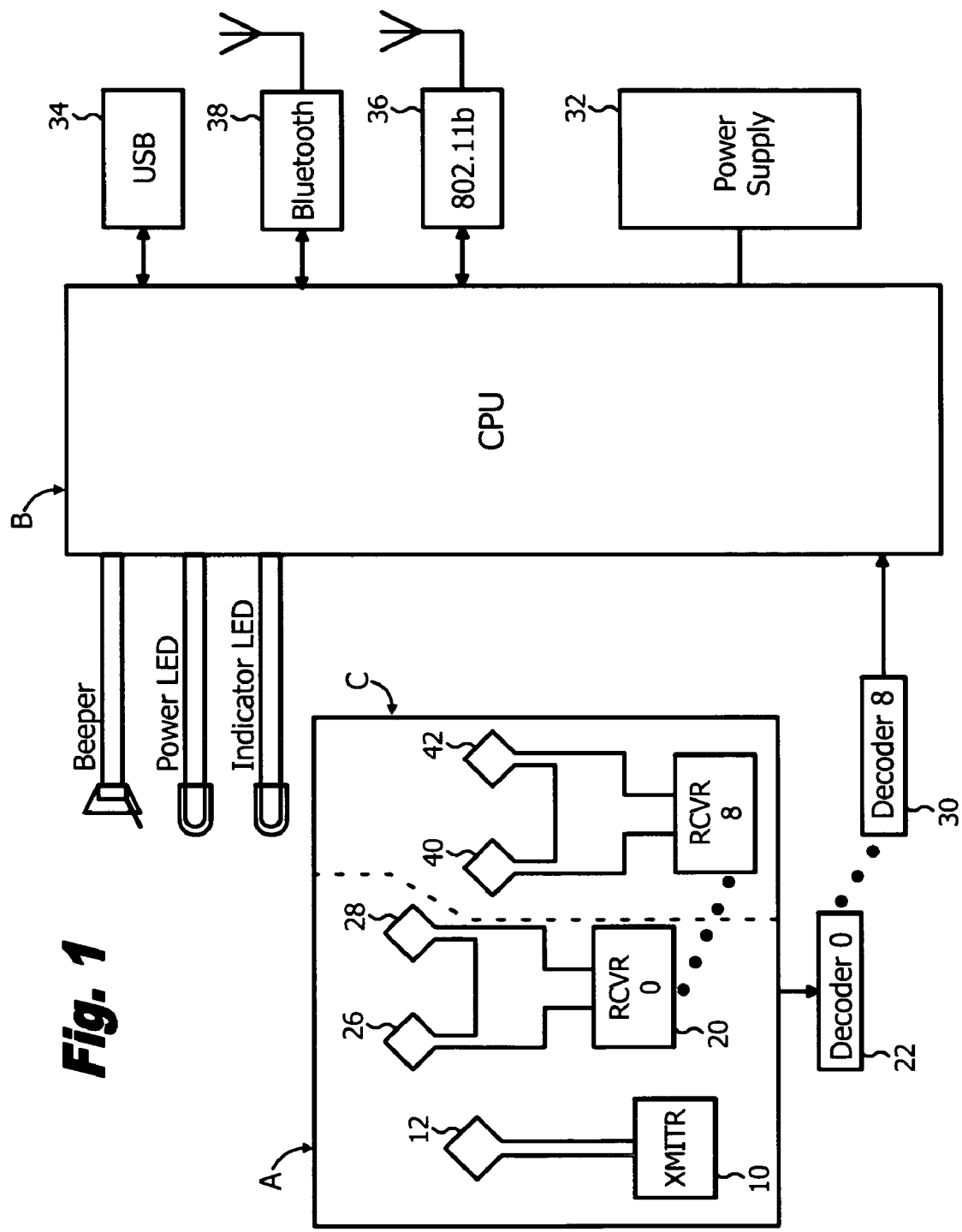
FIG. 1 is a block diagram functionally depicting the components of the system of the present invention.

The basic system configuration is illustrated in FIG. 1 which is a block diagram of the system hardware. The system hardware consists of a transducer, generally designated A, in the form of a hand-held scanner or wand. Transducer A includes a transmitter 10 which preferably takes the form of a high power 128K oscillator. The power output of transmitter 10 is preferably approximately 25 Watts. The output of transmitter 10 is connected to a transmit antenna 12.

Transducer A is connected to a CPU, generally designated B containing the signal processing circuitry. CPU B controls the transmitter on/off cycling. It also coverts the decoded PSK signal into an RS-232 interface. Only a single CPU B is schematically depicted in FIG. 1 for interfacing with each of the signal decoders. However, each decoder may be provided with a separate embedded signal processing circuitry.

Figure 2:
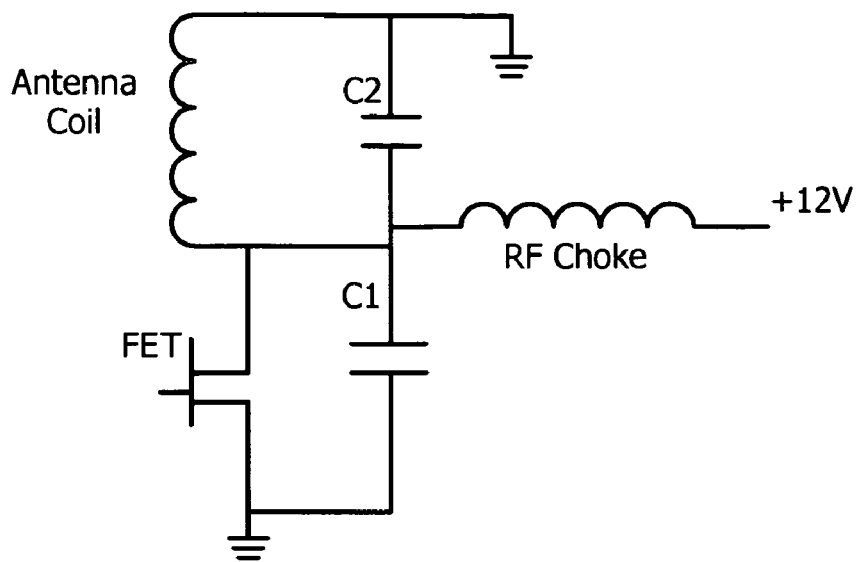
FIG. 2 is a schematic diagram of a conventional single coil antenna.
Figure 3:
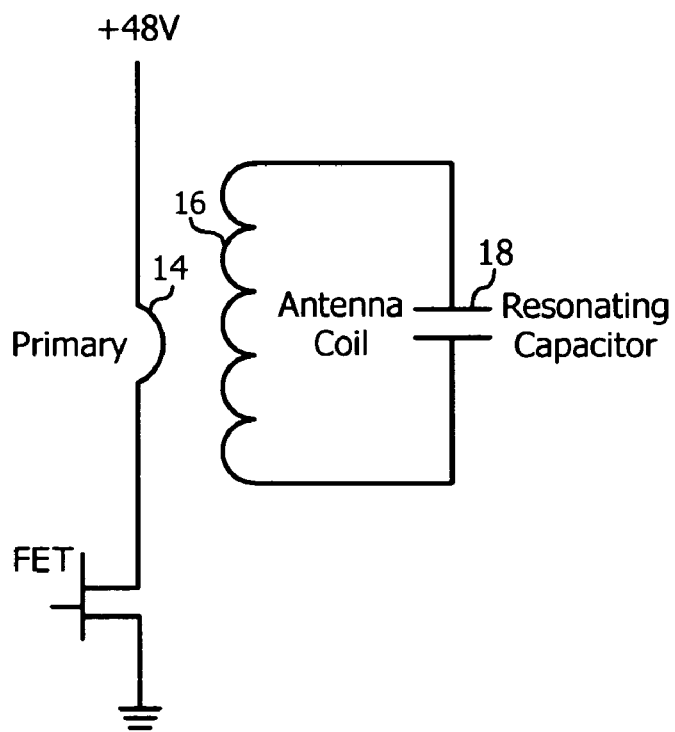
FIG. 3 is a schematic diagram of the configuration of a conventional dual coil transformer.

The transmitter PCB can be configured to drive a transmit antenna which may take the form of a conventional signal coil antenna (FIG. 2) or the dual coil (primary and auxiliary) transformer configuration (FIG. 3). In both cases, the transmit antenna will be wound using up to 30 turns of 550/44 (550 strands of AWG 44) Teflon of PVC coated litz wire, wound on a non-conductive, rigid, lightweight frame. Because litz wire is made up of many stands of fine copper wire, it has much lower resistance to RF currents, and therefore low resistance. Low resistance means a HI-Q circuit can be achieved. It is desired to generate as high a voltage as possible across the antenna.

The preferred embodiment of the present invention uses the dual coil configuration. As shown in FIG. 3, the primary 14 has 1 turn and the auxiliary 16 preferably has 30 turns of litz wire. Voltages as high as 3600V P-P have been recorded in the dual coil antenna.

However, the single coil antenna of FIG. 2 could also be utilized. The transmitter circuit for a single coil antenna 14 is arranged as a modified collpits oscillator, i.e. the junction of two series capacitors is the feed (Tap) point in the parallel LC tuned circuit. The voltage boost in the tuned circuit is proportional to the ratio of the value of the capacitors. The FET is turned on for 1 µs and draws current thru the cap and antenna coil.

The value of capacitor C1 is much greater than that of capacitor C2. Therefore the value of the two capacitors in series is essentially equal to C2. The tuned circuit then rings at the resonant frequency which is given by the equation:

$$F = \frac{1}{2_\Pi \sqrt{LC}}$$

where C is in farads, and L is in Henries and F is in hertz.

In the transmitter for dual coil antenna of FIG. 3, the multi-turn auxiliary 16 is wound with litz wire; a single turn of copper tape is the primary 14. A one-microsecond pulse of high current goes through the primary turn. The magnetic flux generated induces current in the auxiliary 16, which rings according to the resonant frequency of the auxiliary 16 and the capacitor 18 across it. Because all the current is forced to go though the primary of the transformer, this arrangement will deliver power to the antenna at a much better efficiency then the single coil antenna.

It is known that the range along the axis of a loop antenna is proportional to the diameter of the antenna. Therefore, the transmit antenna 12 in the transmitter portion of the transducer should be as large as practical. An 18" to 20" diameter antenna is a good compromise between range and usability. A transmit antenna 12 with a diameter of 18" is used in the preferred embodiment.

Transducer A also includes a receiver 20. Receiver 20 detects the signal coming from the RFID tag transmit coil excited by the signal from transmit antenna 12 of the transducer. This signal is a 64 KHz PSK modulated signal, which carries the coded RFID tag data. The receiver includes a 128 kHz notch filter to reject 128 kHz excitation signals. The 64 kHz signal is allowed through, scaled, and then passed to the decoder 22.

Because the receiver antenna in the transducer is in close proximity to the high power transmit antenna 12, a way of avoiding generating high currents in the receiver antenna at the transmit frequency must be provided. This is accomplished by forming the receiver antenna in the transducer of two substantially identical receiver antennae 26, 28 connected in series, with one of the antennae flipped over so that the received signal in the second antenna is 180 degrees out of phase with the first antenna. This arrangement effectively nulls out any signal from the transmit antenna 12.

Each receive antennae 26, 28 in transducer A consists of 200 runs of AWG 41 magnet wire on an 8"×⅛" disk. A shielded coax connects the antenna output to receiver circuit 20.

The system has nine decoder circuits in all. One decoder circuit 22 interfaces with the transmitter antenna 12 and the receive antennae 26, 28 that are packaged together in the transducer. The other eight decoder circuits 30 respectively interface with different ones of each of the eight auxiliary receiving antennae pairs that form the auxiliary antenna array, generally designated C.

The decoder 22, which is connected to the transmit antenna 12, controls the transmitter on/off by means of a 0-12 vdc, 5 hz, 50% duty cycle control signal. During the on time, transmitter 10 generates a 128 kHz signal. A 128 kHz pulse train, synchronous to the 128 kHz transmit signal, is provided to decoder 22 to synchronize the received signal.

Each decoder 30 connected to an auxiliary receive antennae pair in array C receives the RF signal from the transmit coil of the RFID tag, generally designated D. That signal is PSK modulated. The decoder circuitry filters, amplifies, and demodulates the PSK signal. The result is passed to the signal processing circuitry of CPU B. The quality of the decoding process is one of the factors that determine the range of the system. The accuracy of the decode process is assured in the present invention because transducer A transmits the code twice and the signal processing circuitry will only indicate the presence of a RFID tagged object in the body when both received code transmissions match.

A power supply 32 is provided for the auxiliary antenna array C and the associated electronics, including CPU B. The power supply 32 must supply 48VDC to achieve high power in the antennae. Power supply 32 may be connected to receive either 120VAC line current or to batteries with a boost voltage DC-DC converter.

CPU B is optionally connected to a USB port 34 that allows the system to be controlled by a USB master, such as a standard PC (not shown). The system will have the standard USB type slave connector on it. Since the data rate is low, the USB port can be designed around a USB to RS-232 chip, which make for easy integration.

A RS-232 to wireless interface chip 36 can be used. Similarly, a RS-232 to Bluetooth interface chip 38 can be used.

Figure 4:
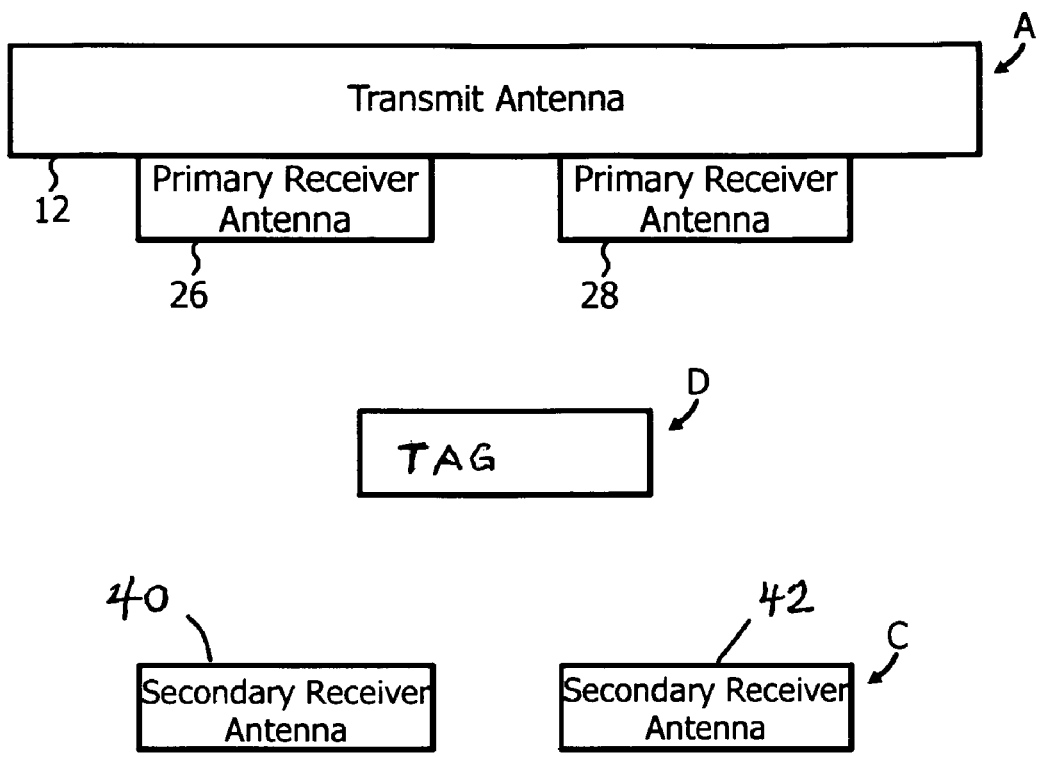
FIG. 4 is a block diagram of the RF signal transducer, tagged object and auxiliary antenna array of the present invention.
Figure 7:
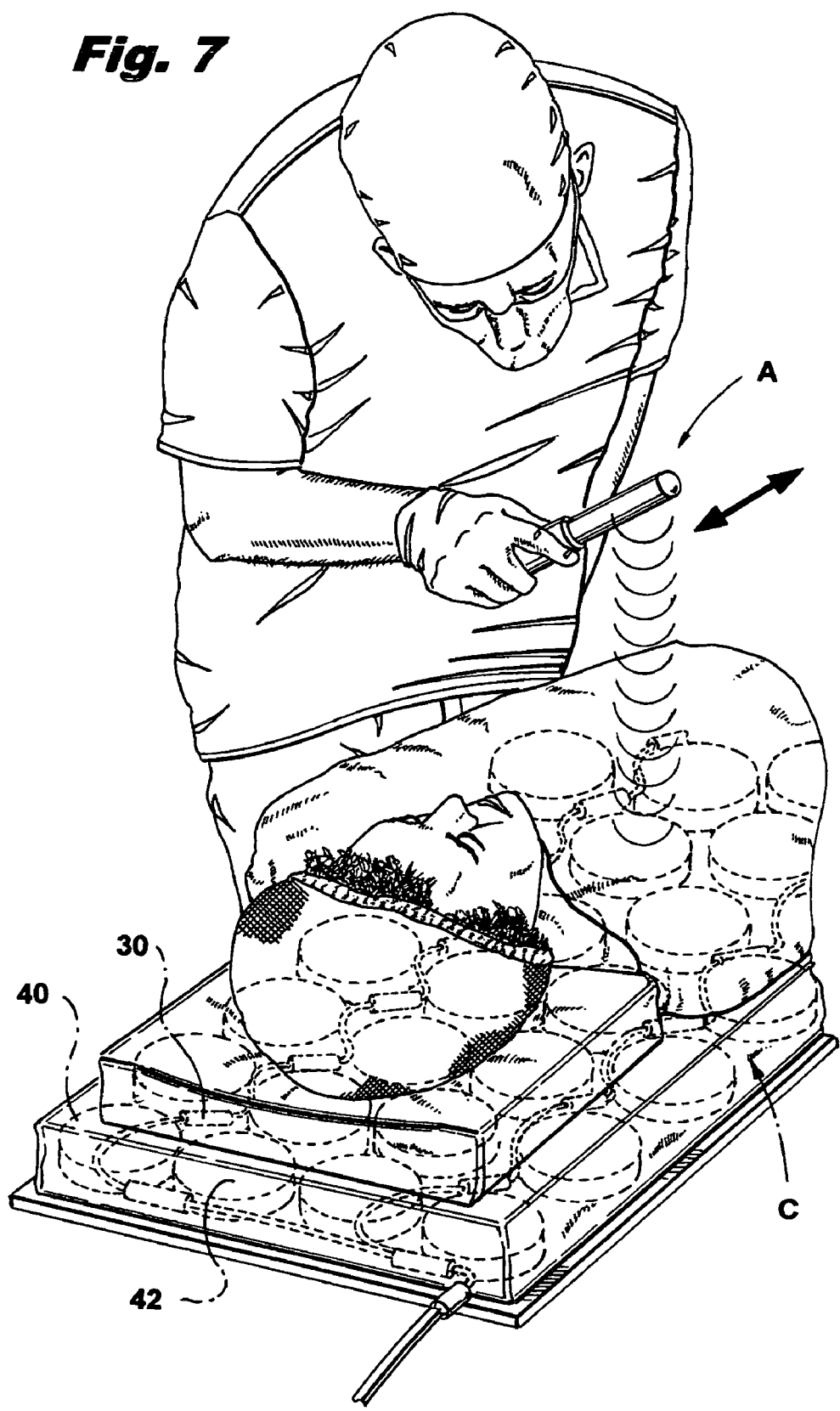
FIG. 7 is an environmental view showing the scanning process using the auxiliary antenna array of the present invention.

FIG. 4 illustrates the positioning of auxiliary receive antenna array C relative to transducer A and RFID tag D. As shown in that figure, the body of the patient that is being scanned to detect a retained object with a RFID tag D is situated between transducer A and auxiliary RF receive antenna array C. For best results, transducer A is moved in a plane approximately 19 inches from the plane of the antennae of array C. FIG. 7 depicts the scanning procedure using the auxiliary antenna array.

Figure 5:
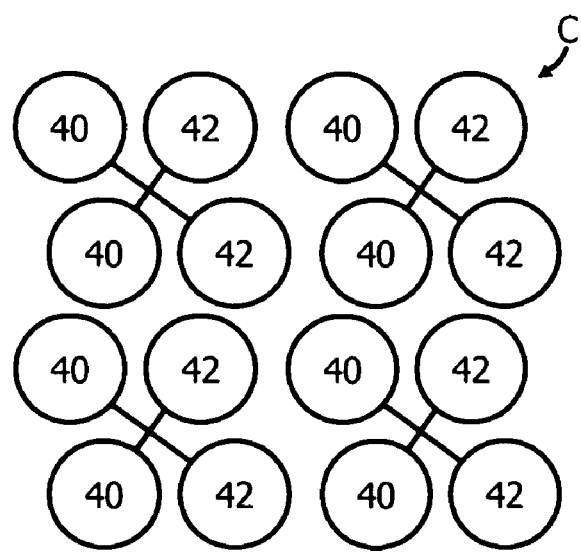
FIG. 5 is a diagram illustrating one preferred layout of the antennae in the auxiliary antenna array of the present invention.
Figure 6:
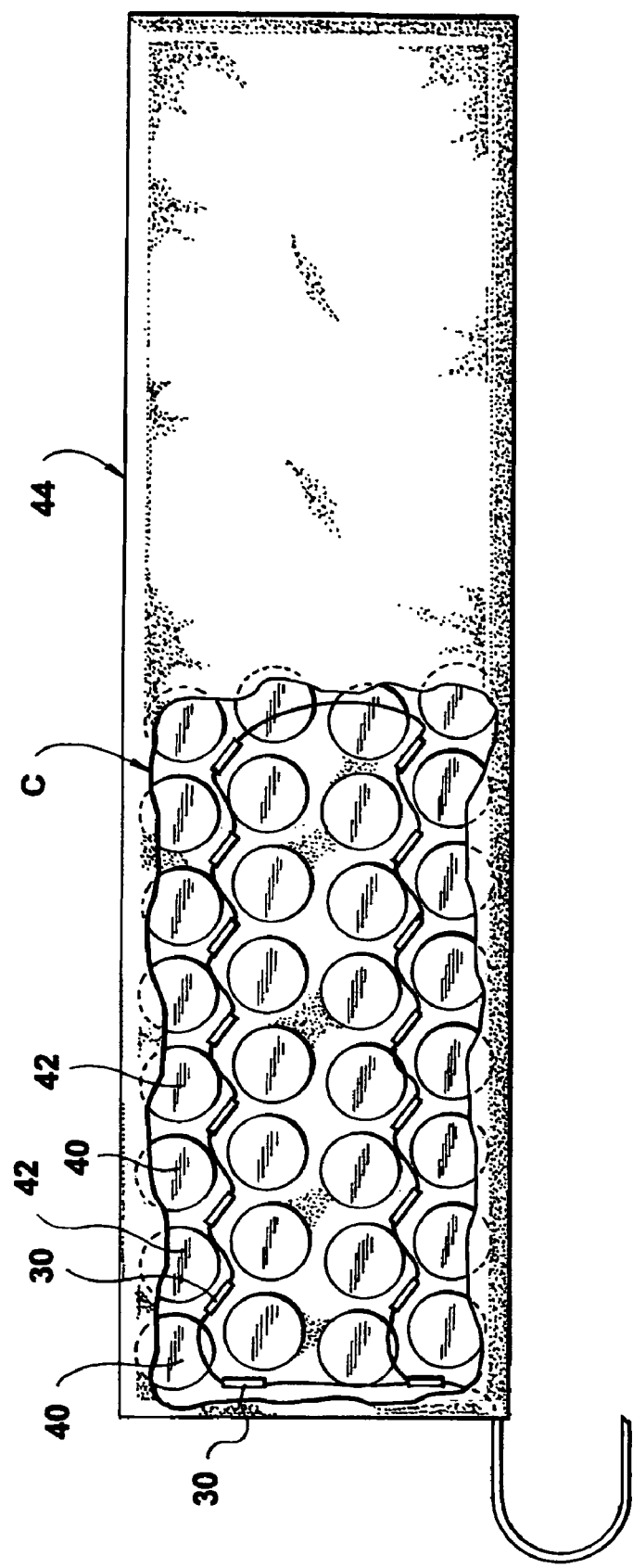
FIG. 6 is an elevation view of a mattress with the auxiliary antenna array of the present invention.

As depicted in FIGS. 5, 6 and 7, array C consists of a plurality of antenna pairs 40, 42 and associated decoders 30. The array is situated at a distance from the transmit antenna 12 in transducer A so as to extend the range of the system.

The antenna pairs 40, 42 and decoders 30 of array C are preferably embedded in the upper half a mattress 44 made of insulating material such as foam rubber. Mattress 44 is designed to be placed on top of the operating table so as to align the array with the torso of the patient. Each pair of antennae 40, 42 in the array is connected to a different decoder 30. This arrangement greatly increases the overall range of the system.

The individual receiving antennae 40, 42 in the array are preferably toroidal. The coils are 3 to 10 inches in diameter, with a thickness of less than 1 inch. The coils are wound on custom coil forms constructed of insulating material. The insulating material may be made by laminating multiple pieces of plastic such as glass filled epoxy board used in the fabrication of printed circuit boards. The coils can also be constructed as multilayer printed circuit boards. The form material may also be semi-rigid so that the coil assemblies can flex.

Preferably, the antennae in array C are arranged in rows extending along the length of upper portion of mattress 44, as illustrated in FIG. 6.

It will now be appreciated that the present invention relates to a system for detecting foreign objects in a patient on an operating table that includes a hand-held transducer capable of reading RFID tags through a human body at a distance of up to 14 inches from the body. The design of the auxiliary antenna array provides reliable reception of the signal from the RFID tag no matter what the orientation of the object is. One pass of the hand-held transducer with the receive antennae from head to toe of the patient should detect any RFID tagged objects that are in the patient's body. A visual and audible signal indicating a detection of the RFID tagged object is provided. Optionally, the signal processing circuitry may connect the read RFID tag data to a PC through USB, wireless Bluetooth or 802.11b connection.

While only a single preferred embodiment of the present invention has been disclosed for purposes of illustration, it is obvious that many modifications and variations could be made thereto. It is intended to cover all of those modifications and variations which fall within the scope of the present invention, as defined by the following claims.

I claim:

1. Apparatus for detecting an RFID tagged object in the body of a surgical patient situated on an operating table, the apparatus comprising: RF transducer means situated above the body of the surgical patient, said transducer means comprising means for generating a signal for energizing a RFID tag associated with an object situated within the body of the surgical patient to transmit an RF signal and antenna means for receiving said RF signal from said RFID tag energized by said energizing signal; a mattress pad situated under the body of the surgical patient; auxiliary antenna means located within said mattress pad remotely from said RF transducer means for receiving said RF signal from said RFID tag energized by said energizing signal; said transmitted RF signal; and signal processing means operably connected to said antenna RF signal receiving means and said auxiliary antenna means for determining when an RF signal from said RFID tag energized by said energizing signal has been received by either said antenna means or said auxiliary antenna means.

2. The apparatus of claim 1 wherein said antenna means is associated with said RF transducer means.

3. The apparatus of claim 1 wherein said RF transducer means comprises a hand-held scanner.

4. The apparatus of claim 1 wherein the body of the patient is situated between said antenna means and said auxiliary antenna means.

5. The apparatus of claim 1 further comprising means operably connected to said signal processing means for indicating the receipt of a RF signal from said RFID tag.

6. The apparatus of claim 5 wherein said indicating means generates an audible signal.

7. The apparatus of claim 5 wherein said indicating means generates a visible signal.

8. The apparatus of claim 1 wherein said RFID tag is a small, low frequency RFID tag.

9. The apparatus of claim 1 wherein said RF signal comprises coded data identifying the object associated with the RFID tag from which the RF signal is received and further comprising means for decoding said coded data to identify the object associated with said RFID tag generating said RF signal.

10. The apparatus of claim 1 wherein said antenna means comprises a pair of substantially identical RF signal receiving antennae connected in series such that a RF signal received in one of said antenna is 180 degrees out of phase with the RF signal received by the other of said antenna.

11. The apparatus of claim 1 wherein said auxiliary antenna means comprises first and second RF signal receiving antennae.

12. The apparatus of claim 1 wherein said RF signal comprises coded data identifying the object associated with the RFID tag from which the RF signal is received and wherein said antenna means comprises means for decoding said coded data to identify the object with said RFID tag from which the RF signal is received.

13. The apparatus of claim 12 wherein said auxiliary antenna means comprises first and second RF signal receiving antenna pairs and said decoding means comprises first and second decoders, each of said first and second decoders being respectively operably connected to a different pair of said RF signal receiving antennae.

14. The apparatus of claim 1 wherein said auxiliary antenna means comprises an antenna array.

15. The apparatus of claim 14 wherein said array comprises a plurality of toroidal antennae.

16. The apparatus of claim 15 wherein said antennae are situated in rows.

17. The apparatus of claim 16 wherein said antennae rows are substantially parallel.

18. The apparatus of claim 14 wherein said antenna array is located in the upper portion of said mattress pad.

19. Apparatus for identifying an RFID tagged object in the body of a surgical patient, the apparatus comprising: RF transducer means located above the body of the patient comprising means for energizing a RFID tag to transmit a RF signal including coded data identifying the object with which said transmitting RF tag is associated and first means for receiving and decoding said transmitted RF signal; second means located below the body of the patient for receiving and decoding said transmitted RF signal; and signal processing means operably connected to said first receiving and decoding means and to said second receiving and decoding means for identifying the object associated with said RFID tag transmitting the received RF signal, further comprising a mattress pad, wherein said second receiving and decoding means comprises an antenna array located in said mattress pad.

20. The apparatus of claim 19 wherein said signal processing means comprises means for identifying the object associated with the RFID tag transmitting the received RF signal.

21. The apparatus of claim 19 wherein said RF transducer means comprises a hand-held scanner.

22. The apparatus of claim 19 wherein the body of the patient is situated between said first receiving and decoding means and said second receiving and decoding means.

23. The apparatus of claim 19 further comprising means operably connected to said signal processing means for indicating receipt of a RF signal from said RFID tag.

24. The apparatus of claim 19 wherein said RFID tag is a small, low frequency RFID tag.

25. The apparatus of claim 19 further comprising a mattress pad within which said second receiving and decoding means is located.

26. The apparatus of claim 19 wherein said second receiving and decoding means comprises a pair of RF signal receiving antennae.

27. The apparatus of claim 19 wherein said second receiving and decoding means comprises first and second pairs of RF signal receiving antennae.

28. The apparatus of claim 27 wherein said second receiving and decoding means comprises first and second decoders, a different one of said decoders operably connected to each said RF signal receiving antennae pair.

29. The apparatus of claim 19 wherein said second receiving and decoding means comprises first and second decoders.

30. The apparatus of claim 19 wherein said array comprises a plurality of toroidal antennae.

31. The apparatus of claim 30 wherein said antennae are situated in rows.

32. The apparatus of claim 31 wherein said antennae rows are substantially parallel.

33. The apparatus of claim 19 wherein said antenna array is located in the upper portion of said mattress pad.

34. The apparatus of claim 19 wherein said first RF signal receiving and decoding means comprises first and second oppositely oriented substantially identical antennae connected in series.

* * * * *